(12) United States Patent
Kobayashi et al.

(10) Patent No.: US 12,178,587 B2
(45) Date of Patent: Dec. 31, 2024

(54) NON-TRANSITORY COMPUTER-READABLE RECORDING MEDIUM, ENCEPHALOPATHY DETERMINATION METHOD, AND INFORMATION PROCESSING APPARATUS

(71) Applicant: FUJITSU LIMITED, Kawasaki (JP)

(72) Inventors: Ken Kobayashi, Setagaya (JP); Yuhei Umeda, Kawasaki (JP); Yoshiaki Ikai, Fujisawa (JP); Kazuaki Hiraoka, Funabashi (JP); Tomoyuki Tsunoda, Kawasaki (JP); Yoshimasa Kadooka, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 355 days.

(21) Appl. No.: 16/898,871

(22) Filed: Jun. 11, 2020

(65) Prior Publication Data

US 2020/0397330 A1 Dec. 24, 2020

(30) Foreign Application Priority Data

Jun. 19, 2019 (JP) .................................. 2019-113743

(51) Int. Cl.
*A61B 5/00* (2006.01)
*A61B 5/369* (2021.01)
*G06F 17/14* (2006.01)
*G16H 10/60* (2018.01)
*G16H 50/20* (2018.01)

(52) U.S. Cl.
CPC ............ *A61B 5/369* (2021.01); *A61B 5/7253* (2013.01); *A61B 5/7275* (2013.01); *G06F 17/14* (2013.01); *G16H 10/60* (2018.01); *G16H 50/20* (2018.01)

(58) Field of Classification Search
CPC ..... A61B 5/369; A61B 5/7253; A61B 5/7275; G16H 10/60; G16H 50/20; G06F 17/14
See application file for complete search history.

(56) References Cited

U.S. PATENT DOCUMENTS

2017/0147946 A1 5/2017 Umeda
2019/0200893 A1* 7/2019 Grouchy ............... G06T 3/4007

FOREIGN PATENT DOCUMENTS

JP 2017-97643 6/2017
WO 2015/039689 A1 3/2015

* cited by examiner

*Primary Examiner* — Mohamed Charioui
*Assistant Examiner* — Christine Y Liao
(74) *Attorney, Agent, or Firm* — STAAS & HALSEY LLP

(57) ABSTRACT

A detection device generates plural attractors based on brainwave data. Subsequently, the detection device calculates a Betti number by subjecting the attractors to persistent homology transform. The detection device determines an onset of encephalopathy based on a first order component of a Betti sequence calculated based on the Betti number.

7 Claims, 10 Drawing Sheets

FIG.3
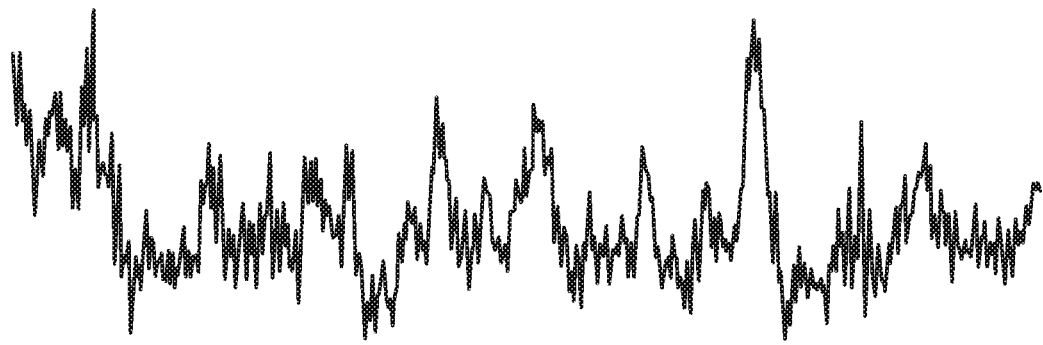
FIG.4
WAVEFORM OF DIFFUSE SLOWING
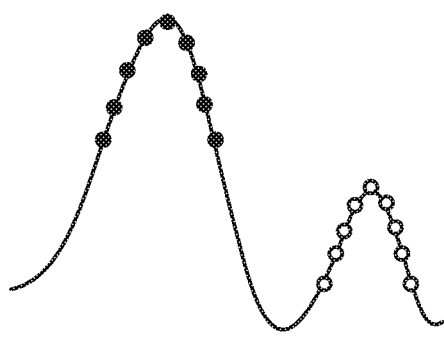
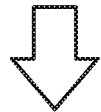
ATTRACTOR
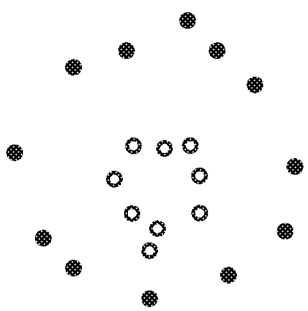

RADIUS: 0

RADIUS: $r_1$

RADIUS: $r_2$

RADIUS: $r_3$

NON-TRANSITORY COMPUTER-READABLE RECORDING MEDIUM, ENCEPHALOPATHY DETERMINATION METHOD, AND INFORMATION PROCESSING APPARATUS

CROSS-REFERENCE TO RELATED APPLICATION

This application is based upon and claims the benefit of priority of the prior Japanese Patent Application No. 2019-113743, filed on Jun. 19, 2019, the entire contents of which are incorporated herein by reference.

FIELD

The embodiment discussed herein is related to a non-transitory computer-readable recording medium, an encephalopathy determination method, and information processing apparatus.

BACKGROUND

Detection of encephalopathy including delirium by detecting a behavior different from normal times by measuring brainwaves of a patient at an early stage has been practiced. Particularly, as the onset of delirium occurs suddenly and the condition continues for several hours to several weeks, early detection is important. Because diffuse slowing, which is a state of low frequency and high amplitude, is observed in brainwaves of most encephalopathies such as delirium, techniques applying frequency analysis or spectrum analysis have been used. In recent years, a detection technique using a tendency that low frequency components pronouncedly appear have also been known (For example, International Publication Pamphlet No. WO 2015/039689, Japanese Laid-open Patent Publication No. 2017-97643).

SUMMARY

According to an aspect of an embodiment, a non-transitory computer-readable recording medium stores therein. an encephalopathy determination program that causes a computer to execute a process. The process includes generating a plurality of attractors based on brainwave data; calculating a Betti number by subjecting the plurality of attractors to persistent homology transform; and determining an onset of encephalopathy based on a first order component in a Betti sequence calculated based on the Betti number.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 3 is an illustration of brainwave data stored in a brainwave data database (DB);

FIG. 4 is an illustration of a waveform portion in diffuse slowing;

DESCRIPTION OF EMBODIMENTS

With the techniques recited in the background section, there are cases in which the detection accuracy of encephalopathy is not high. For example, there are patients, the frequency in diffuse slowing of which is not constant, and there are patients that it does not clearly appear in frequency components. Therefore, which frequency component is suitable for detection vary among individuals, and it is difficult to generalize the settings. Moreover, in diffuse slowing, there is a case in which the low frequency becomes locally high, or a case in which the low frequency band shifts to higher frequencies as a whole, and it can be difficult to be distinguished from an influence of a noise. Under these circumstances, an erroneous detection or omission of detection can occur.

Preferred embodiments will be explained with reference to accompanying drawings. The embodiments are not intended to limit the present invention. Moreover, the respective embodiments may be appropriately combined within a range not causing a contradiction.

[a] First Embodiment

Description of Detection Device

Figure 1:
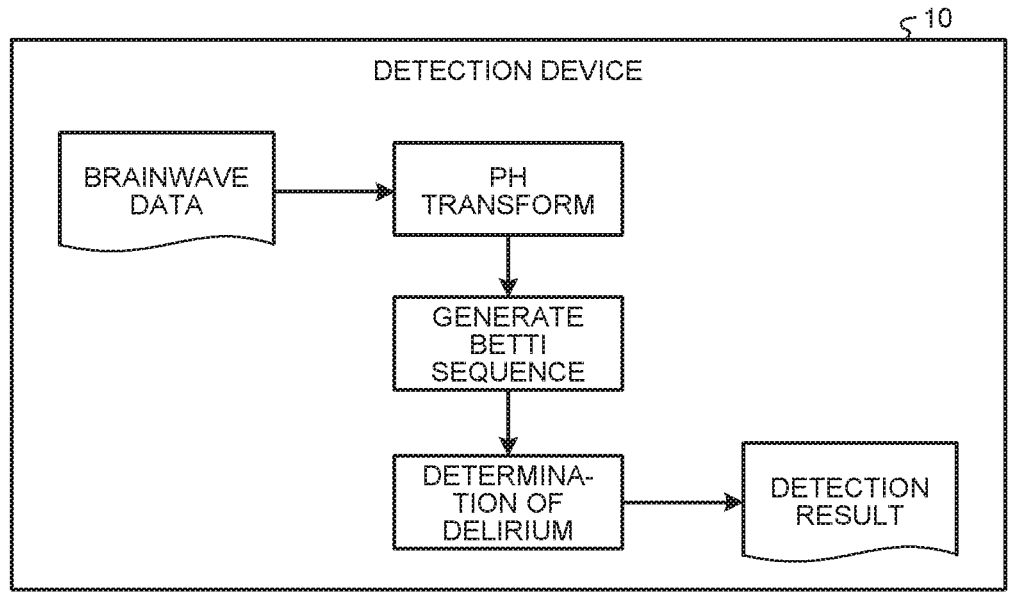
FIG. 1 is an illustration of a detection device according to a first embodiment.

FIG. 1 is an illustration of a detection device 10 according to a first embodiment. The detection device 10 illustrated in FIG. 1 is an example of a computer device that analyzes brainwave data illustrating measured brainwaves of a patient, and that detects encephalopathy including delirium at an early stage. Note that detection of delirium will be explained as an example in the present embodiment.

The detection device 10 according to the first embodiment improves the detection accuracy of delirium by accurately detecting diffuse slowing characterized by many large-amplitude and wide waveforms. The waveforms of diffuse slowing appear as intensities of frequency in the case of regular widths, but there is a case in which they do not appear clearly in the case of irregular widths. The detection device 10 according to the first embodiment enables delirium detection by converting waveforms characterizing delirium into a numerical form, not affected by fluctuations in width of waveforms in brainwave data.

Specifically, as illustrated in FIG. 1, the detection device 10 detects an abnormality in brain data by performing an analysis method using topological data analysis (TAD) on brainwave data of a patient, which is chronological data. For example, the detection device 10 receives brainwave data input thereto, generates a pseudo-attractor that is a limited number of attractor from the brainwave data, and subjects the pseudo-attractor to persistent homology transform (PH transform), to calculate a Betti number. The detection device 10 detects delirium based on a Betti sequence using the Betti number.

Functional Configuration

Figure 2:
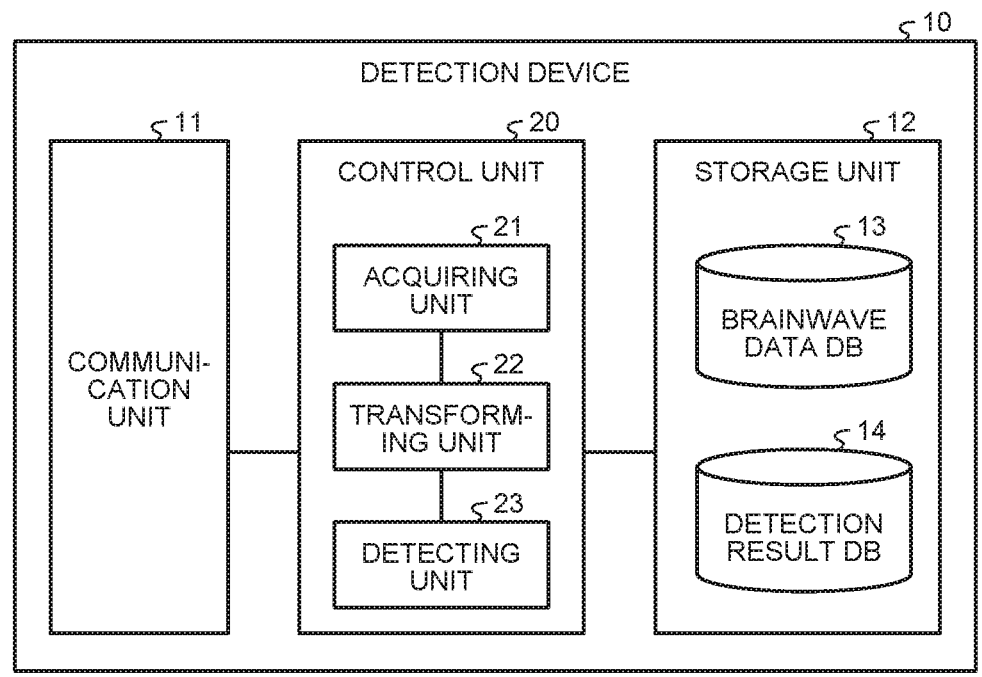
FIG. 2 illustrates a functional configuration of the detection device according to the first embodiment.

FIG. 2 is a functional block diagram illustrating a functional configuration of the detection device 10 according to the first embodiment. As illustrated in FIG. 2, the detection device 10 includes a communication unit 11, a storage unit 12, and a control unit 20.

The communication unit 11 is a processing unit that controls communications with other devices, and is for example, a communication interface, or the like. For example, the communication unit 11 receives brainwave data from measuring instrument that measures brainwaves, receives various kinds of instructions from an administrative device used by a medical staff, and the like, and transmits a detection result of the administrative device.

The storage unit 12 is an example of a storage device that stores various kinds of data, various kinds of programs to be executed by the control unit 20, and the like, and is for example, a memory and a hard disk. This storage unit 12 stores a brainwave data DB 13 and a detection result DB 14.

The brainwave data DB 13 is a database that stores brainwave data indicating brainwaves of a patient measured by the measuring device that measures brainwaves. FIG. 3 is an illustration of brainwave data stored in the brainwave data DB 13. Characteristics of the brainwave data illustrated in FIG. 3 are an example, and its frequency range is 0.5 hertz (Hz) to 30 Hz, its waveform amplitude is 20 microvolts (μV) to 70 μV, and no periodicity is observed. Note that the horizontal axis is for time, and the vertical axis is for amplitude.

The detection result DB 14 is a database that stores a detection result obtained by the control unit 20 described later. Specifically, the detection result DB 14 stores brainwave data and results of delirium detection, associating with respective patients.

The control unit 20 is a processing unit that performs overall control of the detection device 10 and is, for example, a processor or the like. This control unit 20 includes an acquiring unit 21, a transforming unit 22, and a detecting unit 23. The acquiring unit 21, the transforming unit 22, and the detecting unit 23 are an example of processes performed by an electronic circuit included in a processor, or a processor.

Diffuse slowing focused in the first embodiment will be described herein. FIG. 4 is an illustration of a waveform portion in diffuse slowing. As illustrated in FIG. 4, in a waveform portion of diffuse slowing, a waveform of large amplitude appears, and as the number of those portions of large amplitude increases, the severity of delirium increases. Such a waveform of large amplitude forms a circle when an attractor is generated by the TDA processing.

That is, when a waveform of large amplitude is subjected to the persistent homology transform, because a birth time and a death time are both late to make the existing time long, many of first order holes appear, and characteristic are observed in first order components of the Betti sequence. Moreover, because the longer the existing time is, the higher the severity of delirium is, the more the first order components appear, the higher the severity of delirium is. Therefore, in the first embodiment, a pseudo-attractor is generated from brainwave data, and the pseudo-attractor is subjected to the persistent homology transform, to extract first order components of the Betti sequence, and detection of delirium is thereby performed. The first order component of the Betti sequence can also be referred to as a Betti sequence acquired based on a first order Betti number.

The acquiring unit 21 is a processing unit that acquires brainwave data of a patient. For example, the acquiring unit 21 acquires brainwave data of a patient from a measuring device that measures brainwaves, hand stores the brainwave data associated with each patient in the brainwave data DB 13.

The transforming unit 22 is a processing unit that performs PH transform with respect to brainwave data. Specifically, the transforming unit 22 receives brainwave data input thereto, and generates a pseudo-attractor, which is the limited number of attractors, from data divided into segments. The transforming unit 22 then generates plural Betti sequences based on Betti numbers acquired by subjecting each of the pseudo-attractors to the persistent homology transform. The transforming unit 22 outputs the respective generated Betti sequences to the detecting unit 23.

For example, the transforming unit 22 can generate a Betti sequence by using a general method. As an example, the transforming unit 22 divides a section $[r_{min}, r_{max}]$ of a radius to calculate a Betti number into m−1 equal parts, calculates a Betti number $B(r_i)$ of respective radiuses $r_i$ (r=1, ..., m), and generates a Betti sequence $[B(r_i), B(r_1), B(r_2), B(r_3), ..., B(r_m)]$ in which Betti numbers are aligned.

Figure 5:
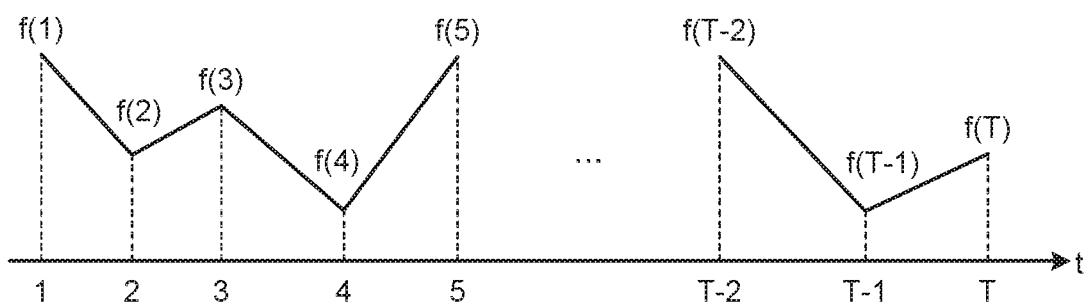
FIG. 5 illustrates as example of chronological data to be a subject.
Figure 6A:
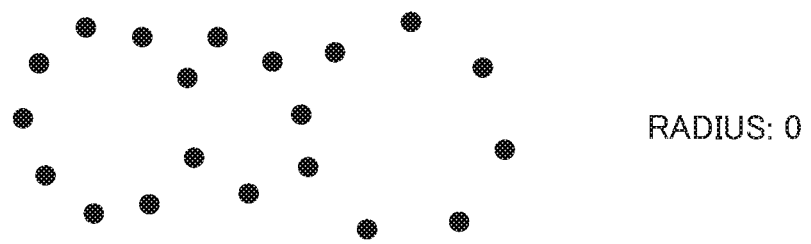
FIGS. 6A to 6D are illustrations of persistent homology.
Figure 6B:
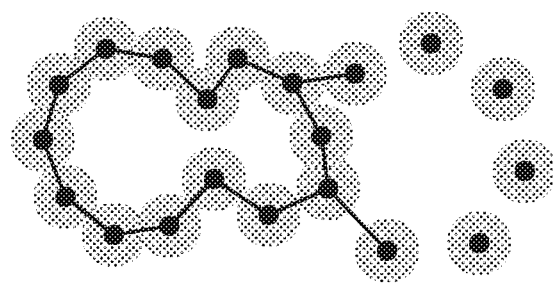
Figure 6C:
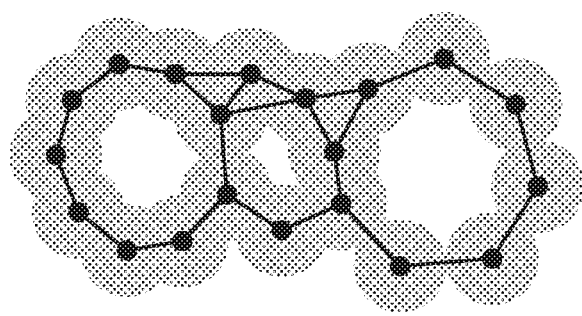
Figure 6D:
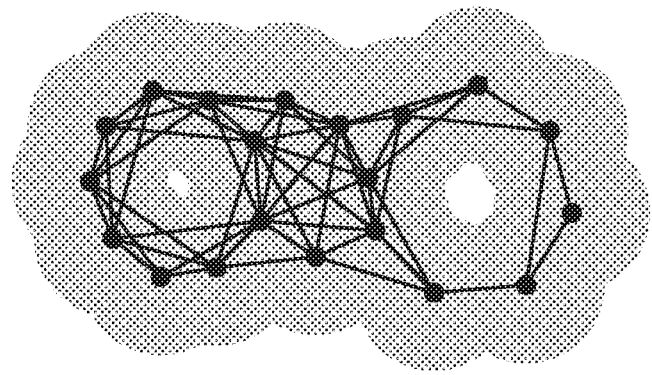
Figure 7:
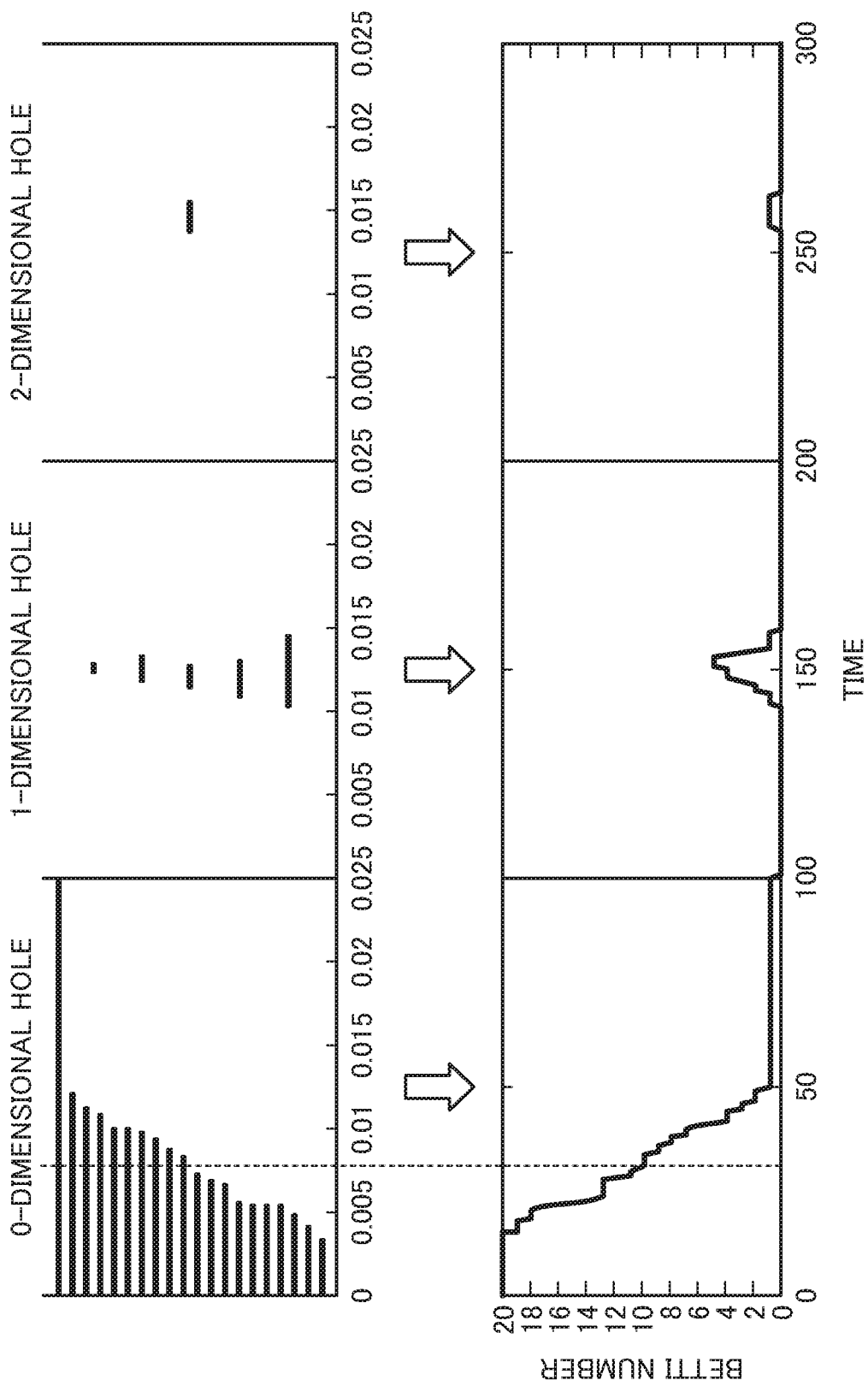
FIG. 7 is a diagram for explaining a relationship between barcode data and successive data to be generated.

The persistent homology transform and generation of a Betti sequence will be described, using FIG. 5 to FIG. 7. FIG. 5 illustrates an example of chronological data to be a subject. FIGS. 6A to 6D are illustrations of persistent homology. FIG. 7 is a diagram for explaining a relationship between barcode data and successive data to be generated.

Generation of a pseudo-attractor will be described, using FIG. 5. For example, successive data expressed by a function f(t) (t indicates time) is considered. Suppose that f(1), f(2), f(3), ..., f(T) are given as actual values. The pseudo-attractor in the present embodiment is a set of points in N-dimensional space having N pieces of values extracted from successive data every delay time τ (τ≥1) as a component. N indicates an embedding dimension, and N=3 or 4 generally. For example, when N=3 and τ=1, following pseudo-attractors including (T-2) points are generated.

pseudo-attractor={(f(1), f(2), f(3)), (f(2), f(3), f(4)), (f(3), f(4), f(5)), ..., (f(T-2), f(T-1), f(T))}

Subsequently, the transforming unit 22 generates a pseudo-attractor, to transform to a Betti sequence by applying the persistent homology transform. The attractor generated herein is referred to as "pseudo-attractor"because it is a set of the limited number of points.

"Homology" is a technique of expressing features of a subject with the number of m-dimensional (m≥0) holes. The "hole" herein is an element of a homology group, and a zero-dimensional hole is a connected component, a one-dimensional hole is a hole (tunnel), and a two-dimensional hole is a void. The number of holes of each dimension is called Betti number. The "persistent homology" is a technique of characterizing transition of an m-dimensional hole in a subject (in this example, point cloud). By using the persistent homology, characteristics of arrangement of points can be determined. In this technique, each point in the subject are gradually expanded into a sphere, and a time at which each hole is generated (expressed by a radius of a sphere at the time of birth) and a time at which a hole disappears (expressed by a radius of the sphere at the time of death) during the expansion are identified.

The persistent homology will be more specifically described by using FIGS. 6A to 6D. As rules, when one sphere comes contact, centers of the two spheres are connected by a line segment, and when three spheres come contact, centers of the three spheres are connected with one another by line segments. Herein, attention is paid only to connected components and holes. In a case of (radius r=0) in FIG. 6A, only connected components are generated, and no hole have been generated. In a case of (radius r=$r_1$) in FIG. 6B, a hole has been generated, and a part of the connected components have disappeared. In a case (radius r=$r_2$) in FIG. 6C, more holes have been generated, and only one connected component is remained. In a case (radius r=$r_3$) in FIG. 6D, the number of connected component remains 1, and one of the holes has disappeared.

In the calculation process of the persistent homology, a birth radius and a death radius of an element (that is, a hole) of a homology group are calculated. By using the birth radius and the death radius of a hole, barcode data can be generated. The barcode data is generated for each hole dimension. Therefore, by combining barcode data of plural hole dimensions, one block of barcode data can be generated. Successive data is data that represents a relationship between a radius (that is, time) of a sphere in persistent homology and a Betti number.

A relationship between barcode data and generated successive data will be described, using FIG. 7. An upper graph is a graph that is generated from barcode data, and a horizontal axis is for radius. A lower graph is a graph that is generated from successive data (Betti sequence), and a vertical axis is for Betti number, and a horizontal axis is for time. AS described above, the Betti number indicates the number of holes. For example, as the number of holes present at the time of a radius corresponding to a broken line in the upper graph is 10, the Betti number corresponding to the broken line in the lower graph is also 10. The Betti number is counted per block. Note that because the lower graph is a graph of a pseudo chronological data, the values of the horizontal axis themselves do not have meanings.

The detecting unit 23 is a processing unit that detects delirium based on the Betti sequence generated by the transforming unit 22. Specifically, the detecting unit 23 makes a determination regarding presence or absence of delirium according to the number of holes, which are the one-dimensional components out of the Betti sequence acquired from the transforming unit 22.

Figure 8:
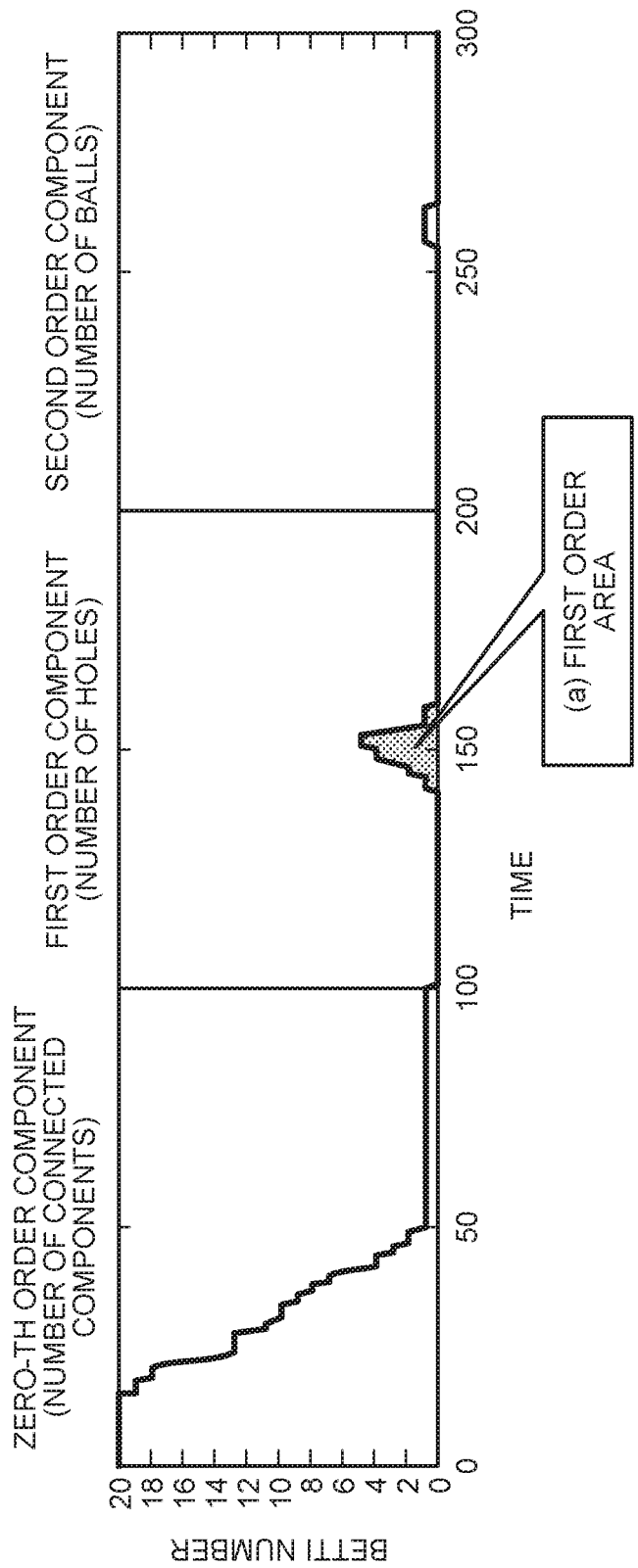
FIG. 8 is a diagram for explaining detection determination of delirium.

FIG. 8 is a diagram for explaining detection determination of delirium. As illustrated in FIG. 8, the detecting unit 23 acquires a one-dimensional Betti sequence from among the Betti sequence generated by the transforming unit 22, and calculates a first order area (score) that is an area of (a) in FIG. 8. Because the horizontal value and the vertical value are known in the graph, the area can be calculated by using a calculation method of various kinds of areas of a rectangle, a trapezoid, a triangle, and the like.

The detecting unit 23 determines that delirium is developed when the area is equal to or larger than a threshold, and determines that delirium is not developed when the area is smaller than the threshold. Thus, the detecting unit 23 detects presence or absence of development of delirium of a patient, and stores a detection result in the detection result DB 14. Moreover, when delirium is detected, the detecting unit 23 notifies of it to a medical staff, and displays the fact on a display or the like.

Furthermore, the detecting unit 23 can be configured to determine that the probability of delirium (determination accuracy) is higher as the area increases. For example, the detecting unit 23 can determine the probability according to the area, determining as probability 1 when the area is larger than a first. threshold, determining as probability 2 when the area is equal to or larger than the first threshold and smaller than a second threshold, and determining as probability 3 when the area is larger than the second threshold.

Flow of Processing

Figure 9:
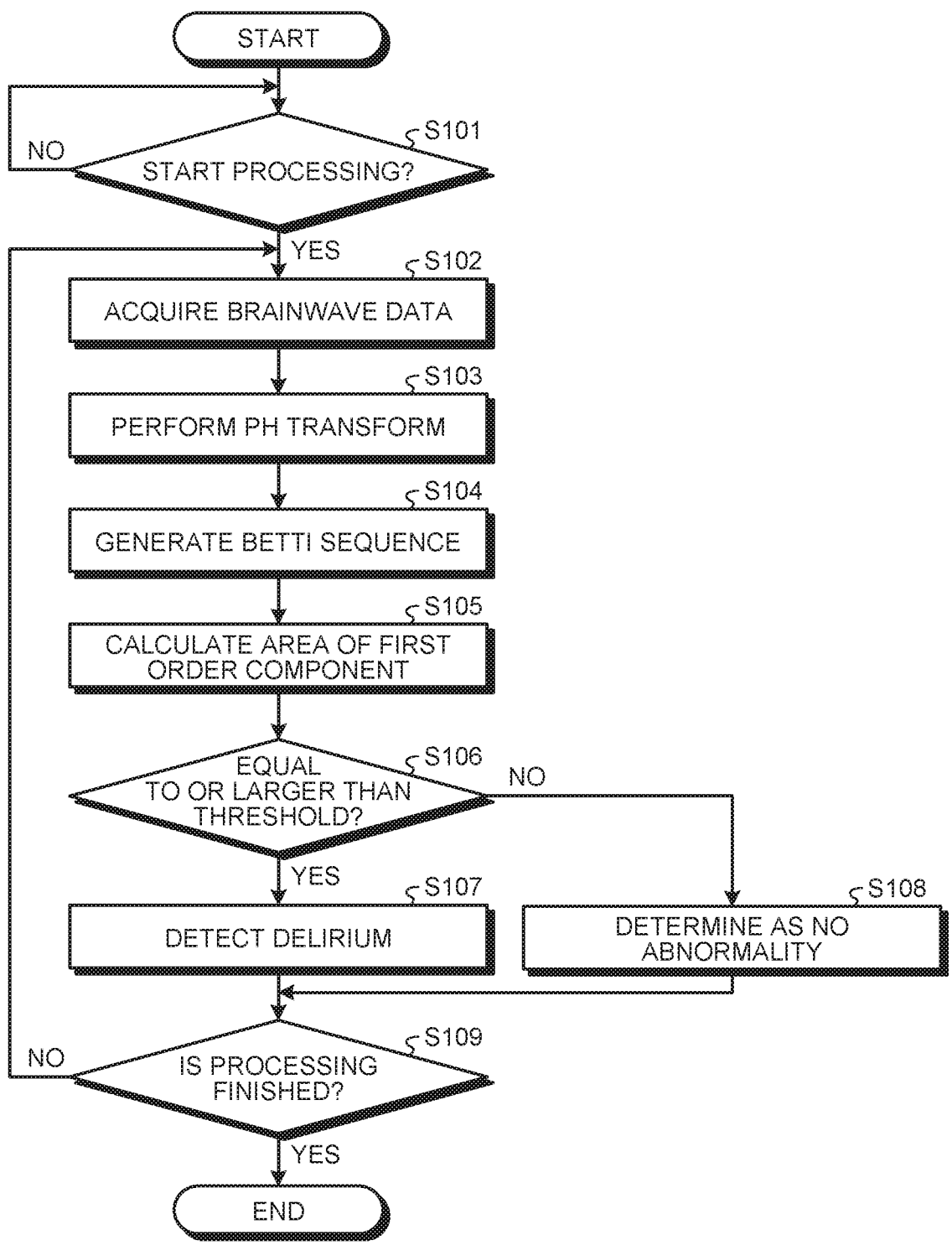
FIG. 9 is a flowchart depicting a flow of processing.

FIG. 9 is a flowchart depicting a flow of processing. Note that it is supposed that the acquiring unit 21 has acquired brainwave data from the measuring device, and has stored it in the brainwave data DB 13.

As illustrated in FIG. 9, when start of processing is instructed (S101: YES), the transforming unit 22 acquires brainwave data of a patient from the brainwave data DB 13 (S102), generates a pseudo-attractor from the brainwave data, and subjects the pseudo-attractor to persistent homology transform (S103). The transforming unit 22 then generates plural Betti sequences by using Betti numbers acquired by the persistent homology transform (S104).

Thereafter, the detecting unit 23 calculates an area of the first order component of the Betti sequence (S105), and when the area is equal to or larger than a threshold (S106: YES), detects symptoms of delirium (S107), and determines, when the area is smaller than the threshold (S106: NO), that no abnormality is observed (S108).

When the processing is continued (S109: NO), the processing at S102 and later is repeated for brainwave data of next patient, and when the processing is finished (S109: YES), the processing of delirium detection is ended.

Effect

As described above, the detection device 10 can perform detection of delirium by generating an attractor from brainwave data, subjecting the attractor to persistent homology transform, and extracting a first order component of a Betti sequence. As a result, the detection device 10 enables delirium detection by converting waveforms characterizing delirium into a numerical form, not affected by fluctuations in width of waveforms in brainwave data and, therefore, can improve the detection accuracy.

Figure 10:
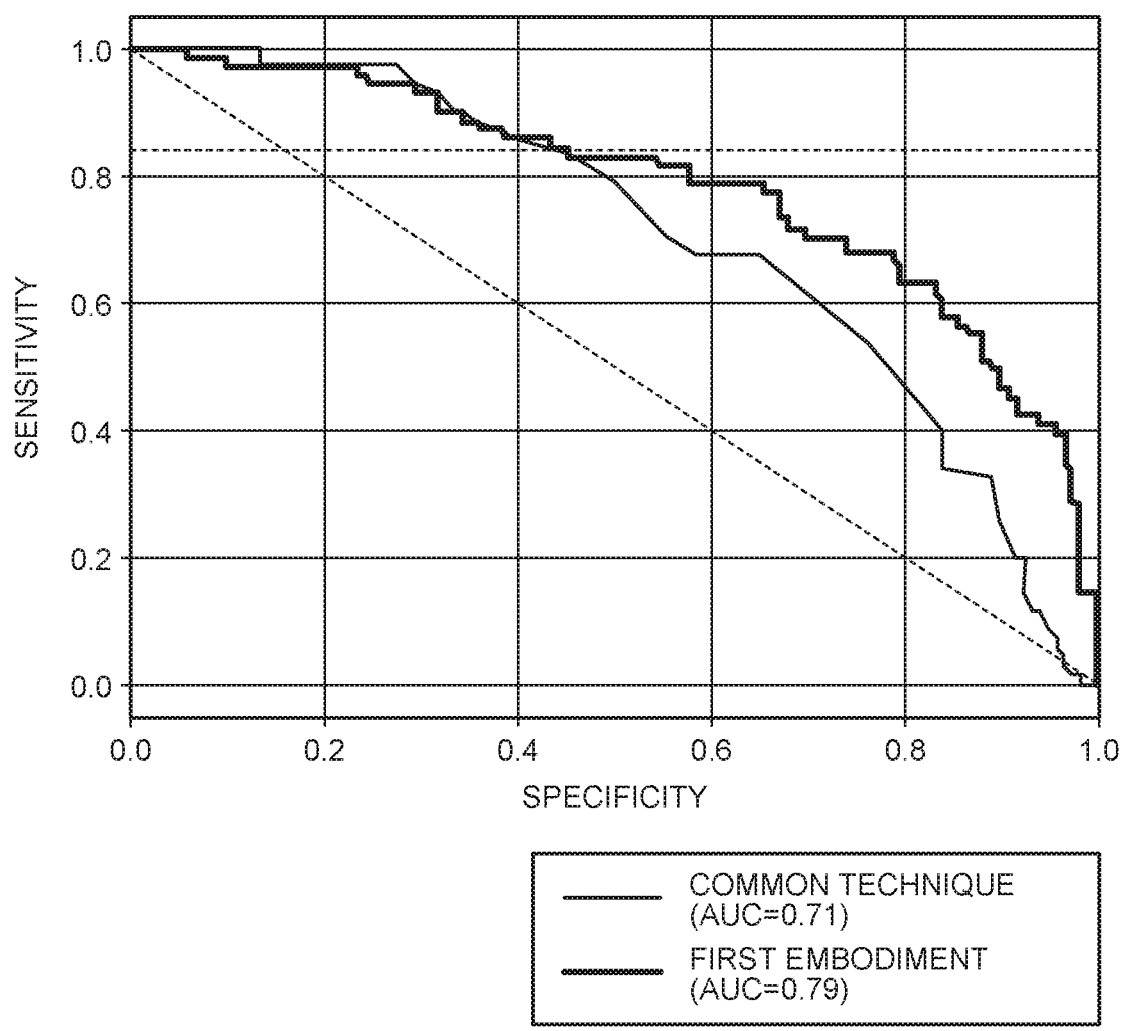
FIG. 10 is a diagram for explaining an effect.

Herein, comparison of detection accuracy between the technique according to the first embodiment and a common technique using frequency analysis and the like will be described by using a receiver operating characteristic (ROC) curve. FIG. 10 is a diagram for explaining an effect. FIG. 10 depicts a relationship between sensitivity that is a rate of accurately catching a person of delirium-positive as positive and specificity that is a rate of accurately determining a person of delirium-negative as negative, by using cases of 78 patients that have developed delirium (positive) and 118 patients that have not developed delirium (negative).

As depicted in FIG. 10, in the common technique, a value of an area under the curve (AUC), which is an area of a lower portion of the graph, is 0.71, and in the first embodiment, the value of AUC is 0.79. AUC takes values from 0 to 1, and indicates that a determination performance is higher as the value becomes closer to 1. Accordingly, the first embodiment has higher accuracy than the common technique. Therefore, by using the technique according to the first embodiment, delirium can be detected more accurately than common frequency analysis in an early stage.

Second Embodiment

The embodiment of the present invention has been described, but the present invention may be implemented by various other embodiments other than the embodiment described above.

Consideration of Weight

Figure 11:
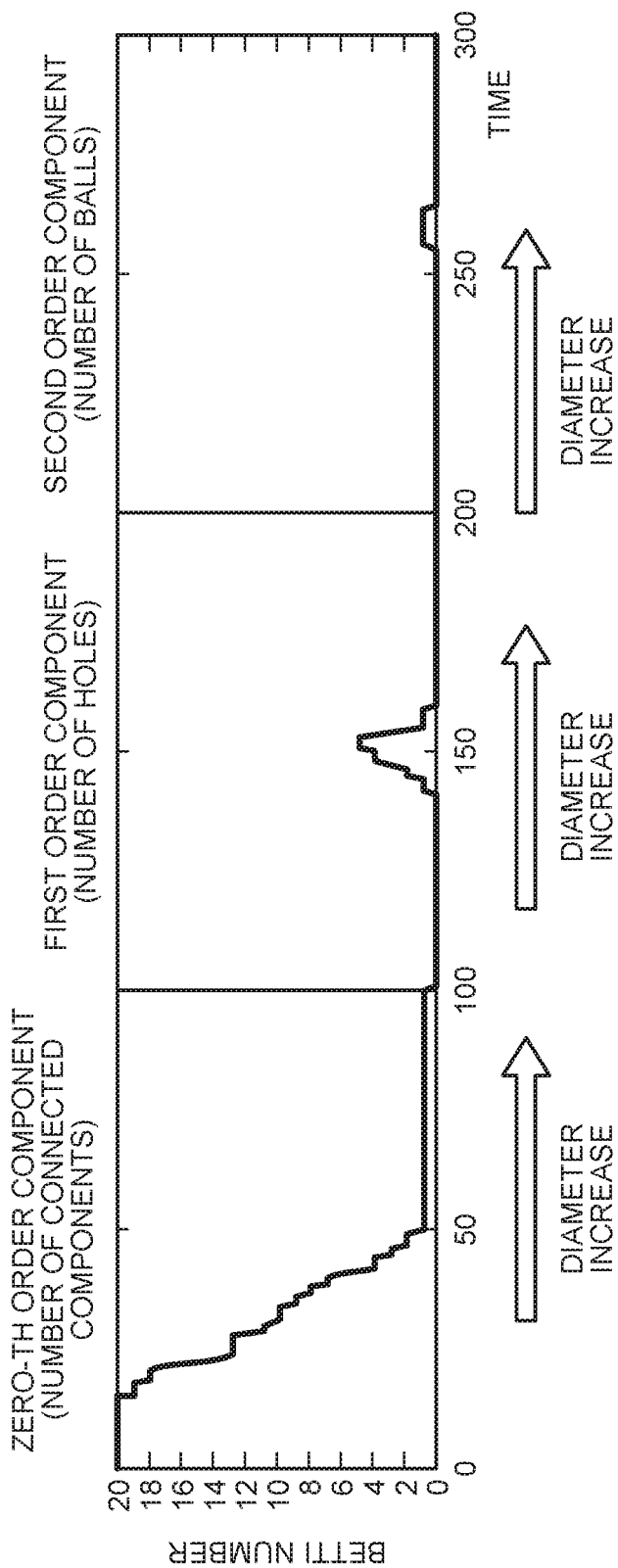
FIG. 11 is a diagram for explaining determination considering a weight.

For example, as the larger the diameter of a primary hole (circle) is, the more the degree (possibility or probability) of delirium is reflected in persistent homology transform, a heavier weight may be assigned to one with a larger diameter, to give importance thereto. FIG. 11 is a diagram for explaining determination considering a weight. As illustrated in FIG. 11, in a Betti sequence generated from barcode data, the diameter of a circle increases as it goes toward right. For example, the detection device 10 sets weights such that a larger weight is assigned to each predetermined range as it goes toward right within a range of a primary Betti sequence. The detection device 10 then multiplies a calculated area by a weight according to an appeared range of the area. The detection device 10 determines that the larger the value obtained after multiplication is, the higher the probability of delirium is.

Separation into Units

Because held information is large in the IDA processing, a too long time series reflects an influence of condition changes of a patient, to cause a noise in delirium determination. For example, soon after a measuring device is put on, a noise is produced by movement of the patient, and also when measurement is continued for a certain length of time, a noise is produced by movement of the patient. For this, to reduce such an influence, a chronological unit length to be converted into a Betti sequence is set to 1 second to 4 seconds, which is comparatively short length while characteristics are observed. Moreover, an area (score) is separated into a unit length to be calculated, and an area that is considered to be an unnecessary influence is removed and scored.

Figure 12:
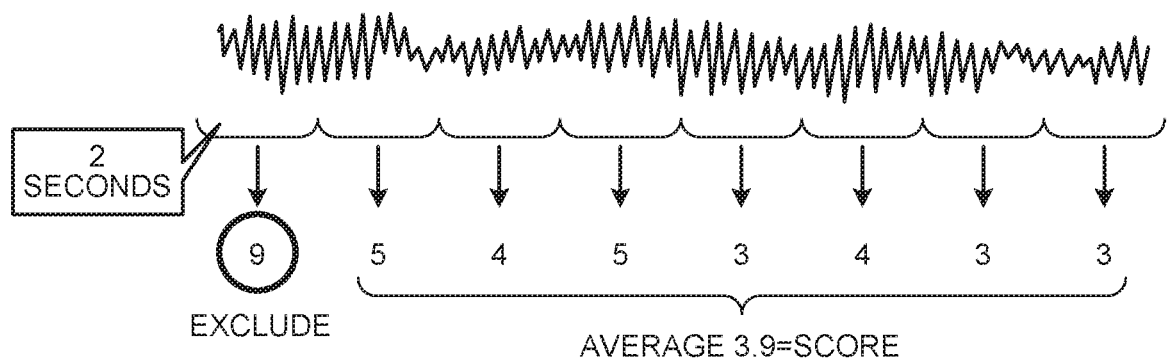
FIG. 12 is a diagram for explaining determination according to segments of unit length.

FIG. 12 is a diagram for explaining determination according to segments of unit length. As illustrated in FIG. 12, the detection device 10 divides brainwave data at intervals of 2 seconds, and subjects brainwave data of each interval to the IDA processing and persistent homology, and then calculates an area of a first order component. The detection device 10 excludes an area that is equal to or larger than a predetermined threshold for determining as noise (for example, 9), and calculates an average value of areas calculated per interval. Thereafter, when the average value is equal to or higher than the threshold, the detection device 10 determines as the onset of delirium.

Data and Numerical Values

The examples of data, numerical values, threshold, displays, and the like used in the above embodiment are only one example, and can be arbitrarily changed. In the first embodiment, a case in which one region is generated in a first order component has been described, but it is not limited thereto. For example, when two or more regions are generated in a first order component, detection of delirium is performed by using a total value of areas of the respective regions. Furthermore, it is possible to assign weights to an area of a region on a right side.

Symptom Determination

For example, when a threshold of area can be set per symptom including delirium, detailed symptoms of encephalopathy can be detected from an area of a first order component. For example, by setting it as a rage between threshold A and threshold B is delirium, an area between threshold B and threshold C is a symptom X, a range equal to or larger than threshold C is a symptom Y in advance, detailed symptoms can be detected.

System

The processing procedure, the control procedure, the specific names, and the information including various kinds of data and parameters described in the above document and the drawings can be changed arbitrarily, unless otherwise specified.

Moreover, the illustrated respective components of the respective devices are of functional concept, and it is not always configured physically as illustrated. That is, specific forms of distribution and integration of the respective devices are not limited to the ones illustrated, and all or a part thereof can be configured to be distributed or integrated functionally or physically in arbitrary units according to various kinds of loads, usage conditions, and the like.

Furthermore, as for the respective processing functions performed by the respective devices, all or an arbitrary part thereof can be implemented by a CPU and a program that is analyzed and executed by the CPU, or can be implemented as hardware by wired logic.

Hardware

Figure 13:
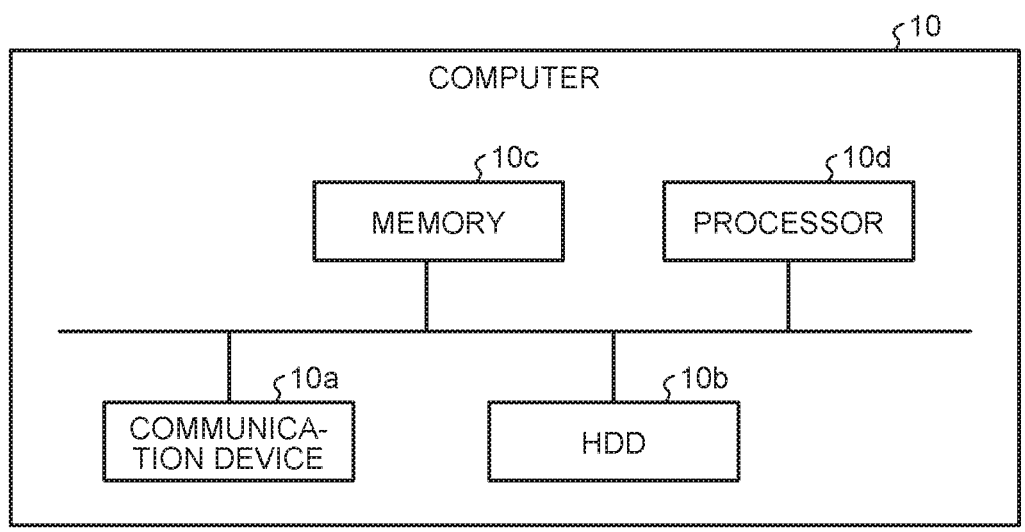
FIG. 13 is an illustration of a configuration example of hardware.

FIG. 13 is an illustration of a hardware configuration example. As illustrated in FIG. 13, the detection device 10 includes a communication device 10a, a hard disk drive (HDD) 10b, a memory 10c, and a processor 10d. Moreover, the respective parts illustrated in FIG. 13 are connected to each other through a bus, or the like.

The communication device 10a is a network interface card, or the like, and performs communication with other devices. The HDD 10b stores a program and a DB to activate the functions illustrated in FIG. 2.

The processor 10d executes a process to implement the respective functions described in FIG. 2 and the like by reading a program to perform processing similar to that of the respective processing units illustrated in FIG. 2, from HDD 10b or the like, and expanding it on the memory 10c. For example, the process implements functions similar to those of the respective processing units included in the detection device 10. Specifically, the processor 10d reads a program having functions similar to those of the acquiring unit 21, the transforming unit 22, the detecting unit 23, and the like from the HDD 10b. The processor 10d then executes the process to implement, the processing similar to those of the acquiring unit 21, the transforming unit 22, the detecting unit 23, and the like.

As described, the detection device 10 operates as an information processing device that performs the detection method by reading and executing a program. Moreover, the detection device 10 can implement functions similar to those in the embodiment described above by reading the above program from a recording medium with a medium reader device, and by executing the read program The program in other embodiments are not limited to be executed by the detection device 10. For example, the present invention can be similarly applied also when the program is executed by another computer or server, or when the program is executed by those in cooperation.

In one aspect, the accuracy of encephalopathy detection can be improved.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A non-transitory computer-readable recording medium having stored therein an encephalopathy determination program that causes a computer to execute a process comprising:
    acquiring brainwave data of a patient;
    generating a plurality of attractors based on the brainwave data;
    calculating a Betti number based on time periods of existence of first order holes occurring by subjecting the plurality of attractors to persistent homology transform;
    determining that an onset of encephalopathy of the patient is developed when an area of a first order component is equal to or larger than a threshold in a Betti sequence indicated by a graph of the Betti number against time; and
    when encephalopathy is detected based on the result of the determining, notifying that the encephalopathy is detected to the medical staff, and displaying the determined result of the onset of the encephalopathy.

2. The non-transitory computer-readable recording medium according to claim 1, wherein
    the determining includes calculating an area of the first order component of the Betti sequence, and determining that the encephalopathy is developed when the area of the first order component is equal to or larger than a threshold.

3. The non-transitory computer-readable recording medium according to claim 2, wherein
    the generating includes the generating a plurality of pseudo-attractors per segment obtained by dividing the brainwave data at predetermined time intervals;
    the calculating includes calculating the Betti number per segment;
    the calculating includes calculating the Betti sequence per segment; and
    determining includes determining that the encephalopathy is developed when an average value of areas of a first order component of the Betti sequence per segment is equal to or larger than the threshold.

4. The non-transitory computer-readable recording medium according to claim 2, wherein
    the determining includes determining that delirium is developed when an area of a first order component of the Betti sequence is equal to or larger than the threshold.

5. The non-transitory computer-readable recording medium according to claim 1, wherein
    the determining includes determining a probability of the encephalopathy according to a size of the area when it is determined that the area of the first order component is equal to or larger than a threshold and the encephalopathy is developed.

6. An encephalopathy determination method comprising:
    acquiring brainwave data of a patient;
    generating a plurality of attractors based on the brainwave data acquired, using a processor;
    calculating a Betti number based on time periods of existence of first order holes occurring by subjecting the plurality of attractors to persistent homology transform, using the processor;
    determining that an onset of encephalopathy of the patient is developed when an area of a first order component is equal to or larger than a threshold in a Betti sequence indicated by a graph of the Betti number against time, using the processor; and
    when the encephalopathy is detected based on the result of the determining, notifying that the encephalopathy is detected to the medical staff, and displaying the determined result of the onset of the encephalopathy.

7. An information processing apparatus comprising:
    a processor configured to:
        acquire brainwave data of a patient;
        generate a plurality of pseudo-attractors based on the brainwave data;
        calculate a Betti number based on time periods of existence of first order holes occurring by subjecting the plurality of attractors to persistent homology transform;
        determine that an onset of encephalopathy of the patient is developed when an area of a first order component is equal to or larger than a threshold in a Betti sequence indicated by a graph of the Betti number against time; and
        notify that the encephalopathy is detected to a medical staff, and display the determined result of the onset of the encephalopathy when the encephalopathy is detected based on the determined result.

* * * * *